United States Patent [19]

Asaoka et al.

[11] Patent Number: 5,382,712
[45] Date of Patent: Jan. 17, 1995

[54] PROCESS FOR THE PRODUCTION OF BISPHENOL A

[75] Inventors: Sachio Asaoka, Yokohama; Tetsuo Maejima, Tokyo; Kouji Sakashita, Tokyo; Noriyuki Yoneda, Tokyo; Makoto Yasui, Yokohama; Nobuhiro Onda, Tokyo; Tsuneo Watanabe, Kawasaki; Nobuo Moriya; Akio Shindo, both of Yokohama; Hiroaki Nishijima, Ebina; Athumi Kukidome, Yokohama; Ryuichi Inaba, Sagamihara; Takashi Imazeki, Ichikawa; Kaoru Shimogawara, Fujisawa, all of Japan

[73] Assignee: Chiyoda Corporation, Yokohama, Japan

[21] Appl. No.: 229,348

[22] Filed: Apr. 18, 1994

Related U.S. Application Data

[62] Division of Ser. No. 912,487, Jul. 13, 1992, Pat. No. 5,324,867.

[30] Foreign Application Priority Data

| Jul. 16, 1991 | [JP] | Japan | 3-201444 |
| Aug. 1, 1991 | [JP] | Japan | 3-216364 |
| Aug. 5, 1991 | [JP] | Japan | 3-219163 |
| Aug. 20, 1991 | [JP] | Japan | 3-232354 |
| Aug. 20, 1991 | [JP] | Japan | 3-232355 |
| Aug. 20, 1991 | [JP] | Japan | 3-232356 |
| Oct. 25, 1991 | [JP] | Japan | 3-306522 |
| Oct. 25, 1991 | [JP] | Japan | 3-306523 |

[51] Int. Cl.$^6$ .................. C07C 37/68; C07C 37/74
[52] U.S. Cl. .................. 568/724; 568/723; 568/722; 568/727
[58] Field of Search ............ 568/724, 723, 727, 728

[56] References Cited

U.S. PATENT DOCUMENTS

| 3,936,507 | 2/1976 | Ligorati et al. | 568/719 |
| 4,327,229 | 4/1982 | Mandiratta | 568/728 |
| 4,894,486 | 1/1990 | Neil, Jr. et al. | 568/702 |
| 4,931,148 | 9/1990 | Immuro et al. | 568/574 |
| 4,942,265 | 7/1990 | Immura et al. | 568/724 |
| 5,324,867 | 6/1994 | Asaoka et al. | 568/724 |

FOREIGN PATENT DOCUMENTS

| 0112615 | 7/1984 | European Pat. Off. |
| 319326 | 6/1989 | European Pat. Off. |
| 0374692 | 6/1990 | European Pat. Off. |
| 4019333 | 6/1963 | Japan |
| 132850 | 4/1988 | Japan |
| 1381398 | 11/1975 | United Kingdom |

*Primary Examiner*—Werren B. Lone
*Attorney, Agent, or Firm*—Armstrong, Westerman, Hattori, McLeland & Naughton

[57] ABSTRACT

High quality bisphenol A is produced from a neutral crystalline adduct of bisphenol A and phenol by fusing the adduct in an atmosphere having a maximum oxygen content of 0.005% by volume, followed by evaporation of liberated phenol. The crystalline adduct may be mixed with an aliphatic carboxylic acid before the fusion to reduce the coloring of the product. When an acidic crystalline adduct is used, the use of a strong alkali salt of an aliphatic carboxylic acid is suitably used. Interior surfaces of the apparatuses for carrying out the fusion and evaporation are desirably washed with an organic solvent to remove oxygen therefrom. The evaporation of phenol is suitably performed by two stage steam stripping wherein a used stripping gas obtained in the second stage is employed as a stripping gas in the first stage while steam is used as the stripping gas in the second stage.

6 Claims, 3 Drawing Sheets

PROCESS FOR THE PRODUCTION OF BISPHENOL A

This is a division, of application Ser. No. 07/912,487 filed Jul. 13, 1992, now U.S. Pat. No. 5,324,867.

This invention relates to a process for the production of bisphenol A.

One well known process for the production of bisphenol A (2,2-bis(4'-hydroxyphenyl)propane, hereinafter referred to as BPA for brevity) includes reacting acetone with a stoichiometrically excess amount of phenol in the presence of an acid catalyst. With respect to the recovery of BPA from the reaction product, a method is known which includes the steps of cooling the reaction product to crystallize a BPA/phenol adduct, and removing phenol from the adduct to leave BPA.

In the above BPA production process, the purity of BPA depends largely on the degree of removal of the phenol from the adduct. Impurities other than phenol contained in the adduct also affect the purity of BPA. For the purpose of removing such impurities from the adduct, a method has been proposed in which the adduct is washed with liquid phenol obtained from the adduct (U.S. Pat. No. 4,942,265). While the purity of BPA obtained by this method is higher than that obtained with the use of industrial grade phenol in the washing of the adduct, the grade of the BPA is not fully satisfactory.

The removal of the phenol from the adduct is generally performed by distillation, extraction or steam stripping. For example, U.S. Pat. No. 3,936,507 discloses a process in which a crystalline adduct of BPA and phenol is melted and the fused product is subsequently vaporized at 180° C. or more under a reduced pressure, the resulting vapors of phenol and BPA being then fractionally condensed to separate and recover the phenol and the BPA. JP-A-63-132850 discloses a process in which a crystalline adduct is heated at 180°-200° C. for the removal, by evaporation, of the phenol and the remaining phenol-containing BPA is subjected to steam stripping. The BPA product obtained by these methods is, however, colored during the heating of the adduct. For example, even when the crystalline adduct to be used as a starting material has a high quality and shows an APHA color of 15 or less, the resulting BPA obtained therefrom by the above methods shows a poor hue with an APHA color of 40 or more.

To cope with this problem of coloring during the heating of the adduct, a method has been proposed in which oxalic acid or citric acid is mixed with a blend of phenol/water/BPA and the mixture is distilled to obtain BPA (JP-B-40-19333). The mixing of thioglycol, glycollic acid, polyphosphoric acid, malic acid, lactic acid or glyceric acid with a phenol/BPA adduct to stabilize BPA is also known (JP-B-47-43937 and U.S. Pat. No. 4,894,486). With these known methods, however, a high grade BPA having a good hue is unable to be produced.

The present invention has been made with the foregoing problems of the conventional processes in view and is aimed at the provision of a process which can produce high grade BPA with excellent hue.

In accordance with one aspect of the present invention, there is provided a process of producing bisphenol A, comprising the steps of:

providing a crystalline adduct of bisphenol A and phenol which has an APHA color of not greater than 15 and which shows a pH of 4.9–5.5 when dissolved in an aqueous methanol solution having a pH of 5;

melting said adduct in an atmosphere having an oxygen concentration of 0.005% by volume or less to obtain a melted adduct; and vaporizing and removing phenol from said melted product to leave bisphenol A.

In another aspect, the present invention provides a process of producing bisphenol A, comprising the steps of:

providing a crystalline adduct of bisphenol A and phenol which has an APHA color of not greater than 15 and which shows a pH of 4.9–5.5 when dissolved in an aqueous methanol solution having a pH of 5;

mixing said adduct with an aliphatic carboxylic acid to obtain a mixture containing 1–100 ppm of the aliphatic carboxylic acid based on the weight of said adduct; and heating said mixture at a temperature of 130°–200° C. under a reduced pressure to vaporize and remove phenol from said mixture and thereby leave bisphenol A.

In a further aspect, the present invention provides a process of producing bisphenol A, comprising the steps of:

providing a crystalline adduct of bisphenol A and phenol which has an APHA color of not greater than 15, which contains a strong acid and which shows a pH of smaller than 5 but not smaller than 4 when dissolved in an aqueous methanol solution having a pH of 5;

mixing said adduct with a salt of an aliphatic carboxylic acid to obtain a mixture, said salt being used in an amount so that said mixture shows a pH of about 5 when dissolved in an aqueous methanol solution having a pH of 5; and heating said mixture at a temperature of 130°–200° C. under a reduced pressure to vaporize and remove phenol from said mixture and thereby leave bisphenol A.

In yet a further aspect, the present invention provides a process of producing bisphenol A, wherein a crystalline adduct of bisphenol A and phenol having an APHA color of not greater than 15 is fed to a melting zone to melt said adduct and the melted adduct is introduced into a separation zone to separate the melted adduct into phenol and bisphenol A by evaporation of the phenol from said melted adduct, said process being characterized in that the interior surfaces of said melting zone and said separation zone which are to be contacted with said melted adduct or the phenol separated from said melted adduct are previously washed with an organic solvent for the removal of oxygen gas entrapped in said interior surfaces so that the interior surfaces have an oxygen content of 10 mmoles (millimoles) or less per 1 m² thereof.

In yet a further aspect, the present invention provides a process of producing bisphenol A, wherein a melted crystalline adduct of bisphenol A and phenol having an APHA color of not greater than 15 is introduced into a separation zone to separate the melted adduct into phenol and bisphenol A by evaporation of the phenol from said melted adduct, said process being characterized in that said separation zone is provided with a member for increasing the area of the surface with which said melted crystalline adduct is to be contacted, and that the interior surface of said separation zone and the surface of said member are previously treated for the removal of oxygen gas entrapped thereon so that the inside surface of said separation zone and the surface of said member have an oxygen content of 10 mmoles or less per 1 m² thereof.

In yet a further aspect, the present invention provides a process of producing bisphenol A, comprising the steps of:

liquefying a crystalline adduct of bisphenol A and phenol to obtain a liquefied adduct containing bisphenol A and phenol;

feeding said liquefied adduct to an evaporating zone and forming said liquefied adduct into a downwardly flowing liquid film while maintaining said evaporating zone at a temperature of 160°–185° C. and a pressure of 15–60 Torr to vaporize and remove phenol from said liquefied adduct and thereby obtain a first product containing bisphenol A and 1–5% by weight of phenol;

introducing said first product into a first stripping zone and forming said first product into a downwardly flowing liquid film while feeding a stripping gas to said first stripping zone, wherein said liquid film of said first product is brought into counter-current contact with said stripping gas at a temperature of 170°–185° C. and a pressure of not higher than 15 Torr to strip phenol and to obtain a second product;

introducing said second product into a second stripping zone and forming said second product into a downwardly flowing liquid film while feeding steam to said second stripping zone, wherein said liquid film of said second product is brought into counter-current contact with said steam at a temperature of 170°–185° C. and a pressure of not higher than 15 Torr to strip phenol and thereby obtain a bisphenol A product and phenol-entraining steam; and feeding said phenol-entraining steam to said first stripping zone as said stripping gas.

In yet a still further aspect, the present invention provides a process of producing bisphenol A, comprising the steps of:

liquefying a crystalline adduct of bisphenol A and phenol, which has an APHA color of not greater than 15 and which shows a pH of 4.9–5.5 when dissolved in an aqueous methanol solution having a pH of 5, to obtain a liquefied adduct containing bisphenol A and phenol;

feeding said liquefied adduct to an evaporating zone and forming said liquefied adduct into a downwardly flowing liquid film while maintaining said evaporating zone at a temperature of 160°–185° C. and a pressure of 15–60 Torr and in an atmosphere having an oxygen concentration of 0.005% by volume or less to vaporize and remove phenol from said liquefied adduct and thereby obtain a first product containing bisphenol A and 1–5% by weight of phenol;

introducing said first product into a first stripping zone and forming said first product into a downwardly flowing liquid film while feeding a stripping gas to said first stripping zone, wherein said liquid film of said first product is brought into counter-current contact with said stripping gas at a temperature of 170°–185° C. and a pressure of not higher than 15 Torr to strip phenol and to obtain a second product;

introducing said second product into a second stripping zone and forming said second product into a downwardly flowing liquid film while feeding steam to said second stripping zone, wherein said liquid film of said second product is brought into counter-current contact with said steam at a temperature of 170°–185° C. and a pressure of not higher than 15 Torr to strip phenol and thereby obtain a bisphenol A product and phenol-entraining steam; and feeding said phenol-entraining steam to said first stripping zone as said stripping gas.

In yet a further aspect, the present invention provides a process for condensing a gaseous mixture of steam, phenol and bisphenol A maintained at a pressure of 30 Torr or less, comprising the steps of:

introducing said gaseous mixture into a first cooling zone maintained at a pressure of 30 Torr or less and such a temperature that said steam is prevented from condensing while a portion of said phenol is condensed, wherein said gas is brought into counter-current contact with a first liquid cooling medium to condense substantially all of said bisphenol A and part of said phenol and thereby obtain a mixed gas containing uncondensed steam and uncondensed phenol, said first liquid cooling medium being phenol or bisphenol A-containing phenol;

introducing said mixed gas into a second cooling zone maintained at a pressure of 30 Torr or less and such a temperature that substantially all of said mixed gas is condensed, wherein said gas is brought into counter-current contact with a second liquid cooling medium to condense substantially all of said mixed gas and thereby obtain a condensate-containing liquid, said second liquid cooling medium being an aqueous solution of phenol.

The present invention will now be described in detail below with reference to the accompanying drawings, in which.

FIRST EMBODIMENT

Figure 1:
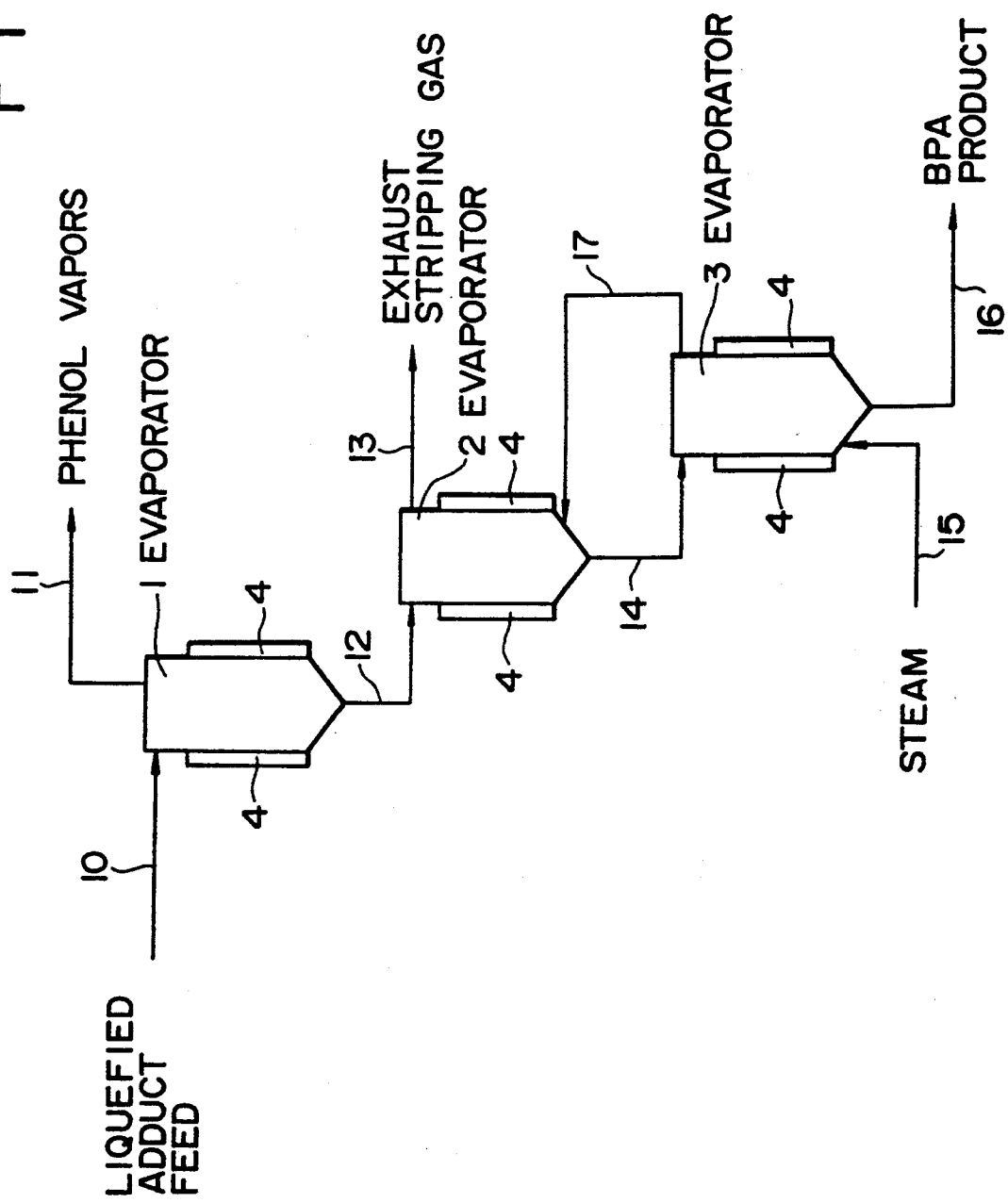
FIG. 1 is a schematic flow diagram showing an apparatus suitable for carrying out a two-stage stripping process of the present invention.

In the first embodiment according to the present invention, a crystalline adduct of BPA and phenol having an APHA color of not greater than 15 and showing a pH of 4.9–5.5 when dissolved in an aqueous methanol solution having a pH of 5 in a concentration of 4 g per ml of water is used as a starting material for the production of BPA.

The reaction of acetone with phenol for the production of BPA is generally performed in the presence of a strongly acidic substance, such as hydrochloric acid, sulfuric acid or a sulfonic acid type ion exchange resin, as a catalyst. These acidic substances, however, serve to facilitate the production of colored substances and impurities at an elevated temperature and thereby reduce the purity of the BPA product. Thus, after the completion of the BPA producing reaction, the acid catalyst is generally neutralized or removed from the reaction mixture so as to avoid the presence thereof in the succeeding phenol removing stage. For example, in a process in which hydrochloric acid is used as catalyst, the reaction mixture after the completion of the BPA producing reaction is heated to remove hydrogen chloride and is then neutralized with an alkali to a pH of 5-6 (JP-B-47-43937). In a process in which a strong-acid type ion exchange resin is used as catalyst, the reaction mixture effluent is contacted with a weak base ion exchange resin to neutralize organic sulfonic acids produced by decomposition of the strong-acid type ion exchange resin during the BPA forming reaction (U.S. Pat. No. 4,191,843). In the above cases, since an alkali adversely affects the purity and color characteristics of BPA and phenol, it is important that the amount of an alkali to be added to the BPA-containing reaction product should not exceed beyond the neutralization point.

Thus, in the production of BPA by reaction of phenol with acetone in the presence of a strongly acidic substance, it is necessary, after the completion of the reaction, to remove the acidic substance or to neutralize the reaction mixture with an alkali. In this case, when an excess alkali is added, it is also necessary to remove the alkali remaining in the reaction product. The removal of the acidic substance or the residual alkali from the reaction product can be performed in a subsequent crystallization step in which BPA produced is crystallized as an adduct with phenol.

The crystalline adduct of BPA and phenol to be used as a starting material in the process of the present invention is of the above-described, neutralized type which is substantially free of such a strongly acidic substance or a residual alkali and which shows a pH of 4.9-5.5, preferably 4.95-5.2 at 20° C. when dissolved in an aqueous methanol solution (water to methanol volume ratio: 5:100) whose pH has been adjusted with hydrochloric acid to 5 in a concentration of 4 g per ml water.

It is also important that the starting material BPA/phenol adduct have an APHA color of not greater than 15, preferably not greater than 10. The term "APHA color" used in the present specification is as measured in accordance with the method specified in ASTM D 1686, "Standard Test Method for Color of Solid Aromatic Hydrocarbons and Related Materials in the Molten State". A crystalline BPA/phenol adduct of the above-mentioned neutralized type generally has an APHA color of 15 or less. Repeated recrystallization of BPA/phenol adduct crystals is effective in controlling the APHA color. It is also effective to wash a BPA/phenol adduct with a purified phenol for decreasing the APHA color.

Any purified phenol may be used for washing the adduct as long as it is substantially free of impurities which would account for the coloring of BPA. Commercially available phenol generally contains an impurity, such as benzofuran and derivatives thereof and aromatic aldehydes and derivatives thereof, which is responsible for the coloring of BPA. Thus, it is essential to remove or reduce such an impurity prior to the use thereof for washing the adduct crystals. Preferably used is purified phenol having an APHA color of not greater than 10, more preferably not greater than 5.

Such a purified phenol may be obtained by a method including the steps of (a) providing raw material phenol which contains impurity, such as mentioned immediately above, capable of forming a high boiling point material having a boiling point of higher than 185° C. when heated at a temperature higher than the melting point of phenol, (b) contacting the raw material phenol with a strong-acid ion exchange resin at such a temperature as to convert at least part of the impurity into the high boiling point material and to obtain treated phenol, and (c) distilling the treated phenol at a temperature of 185° C. or less to separate phenol as distillate from the high boiling point material.

The raw material phenol is preferably selected from (A) phenol for industrial use, (B) phenol separated from a reaction product of phenol and acetone, (C) phenol separated from a crystallization product of BPA-containing phenol and (D) phenol used for washing a crystalline adduct. The raw material phenol preferably has a purity of at least 95% by weight, more preferably at least 97% by weight.

Commercially available phenol of an industrial use grade with a purity of 95% or more may be suitably used as above phenol (A).

After completion of the reaction of acetone with phenol, the product is generally subjected to a separation treatment for removing a part of unreacted phenol therefrom. The phenol thus recovered may be used as raw material phenol (B).

The product obtained by reaction of acetone with phenol is treated to form a crystalline adduct of BPA and phenol. Crystallization is generally performed at a temperature of about 41°-80° C. After crystallization, the mixture is subjected to solid-liquid separation to separate the mixture into a crystalline adduct and a mother liquor. Generally, such crystallization and solid-liquid separation is repeated several times. Thus, phenol is recovered as a mother liquor in each of the solid-liquid separation stages. Such recovered phenol may be used as raw material phenol (C). The phenol recovered in the initial crystallization and separation step is preferably used.

Phenol which has been used for washing the crystalline adduct is recovered. Such phenol may be suitably reused, after being purified, for washing the adduct. Thus, phenol recovered in the washing step may be used as raw material phenol (D).

The purification of above raw material phenol (A)-(D) is performed as follows. The raw material phenol is first contacted with a strong-acid ion exchange resin, generally a sulfonic acid-type ion exchange resin, such as a sulfonated styrene-divinylbenzene copolymer, a sulfonated, cross-linked styrene polymer, a phenol-formaldehyde-sulfonic acid resin or a benzene-formaldehyde-sulfonic acid resin. The ion exchange resin has a cross-linked structure and is insoluble in water. Known sulfonic acid-type ion exchange resins are of a gel-type or a microporous-type. While both types of the ion exchange resins may be used for the purpose of the present invention, the use of a gel-type ion exchange resin is advisable because the activity thereof remains unchanged during use. The gel-type ion exchange resin generally has a degree of cross-linking (the amount of the cross-linking agent contained in the resin) of 10% by weight or less, preferably 5% by weight or less. Illustrative of suitable commercially available, gel-type ion exchange reins are Amberlite, Amberlyst (both manufactured by Rohm & Haas Company) and DIAION (manufactured by Mitsubishi Kasei Inc.).

The contact of the raw material phenol with the ion exchange resin may be carried out by passing the raw material phenol through a fixed layer of the ion exchange packed in a tower or by stirring a mixture of the phenol and the ion exchange resin in a vessel. The contact is generally performed at 45°–150° C., preferably 50°–100° C. for 5–200 minutes, preferably 15–60 minutes. It is preferred that the raw material phenol have a water content of 0.5% by weight or less, more preferably 0.1% by weight or less, for reasons of improved impurity removing effect. The removal of moisture from the raw material phenol may be effected by azeotropic distillation using a suitable known azeotrope agent.

By the contact with the ion exchange resin, the impurities such as benzofuran and derivatives thereof and aromatic aldehydes and derivatives thereof contained in the raw material phenol are converted into high boiling point substances with the ion exchange resin serving as a catalyst.

The raw material phenol which has been treated with the strong-acid ion exchange resin is then distilled to obtain purified phenol as a distillate, with high boiling point impurities formed in the previous treatment with the ion exchange resin being separated as distillation residues.

The distillation is performed under conditions so that the high boiling point impurities are not contained in the distillate. To achieve this purpose, it is preferable to perform the distillation at a temperature of 185° C. or less. At a temperature higher than 185° C., the high boiling point impurities tend to be decomposed and to contaminate the distillate. While the distillation may be carried out at any desired pressure, a reduced pressure of 50–600 Torr is preferably used. The thus obtained purified phenol has a an APHA color of 15 or less so that it does not adversely affect the hue (color characteristics) of BPA when used for washing the adduct of BPA and phenol.

Any method may be adopted for washing the adduct with the purified phenol. For example, after completion of the crystallization for the formation of the crystalline adduct, the adduct is separated from the mother liquor in a solid-liquid separator such as a filtering device or a centrifuge. The purified phenol is fed to the solid-liquid separator for washing the adduct remaining therein. The resulting mixture is then separated into a washed adduct and used phenol. Alternately, the adduct obtained in the solid-liquid separator is transferred to a washing tank where the adduct is washed with the purified phenol with stirring. The washed adduct is again separated with the solid-liquid separator from the used phenol. In either case, the purified phenol is generally used in an amount of 30–1,000 parts by weight, preferably 100–300 parts by weight per 100 parts by weight of the crystalline adduct to be washed. The phenol obtained after the washing of the adduct may be utilized, for example, as a washing liquid for washing a crude BPA/phenol adduct and the resulting washing liquid may be used as at least a part of starting material phenol to be reacted with acetone.

In the process according to the first embodiment, the crystalline BPA/phenol adduct is melted in an atmosphere having an oxygen concentration of 0.005% by volume or less, preferably 0.001% by volume or less, and the resulting melted adduct is vaporized to remove phenol therefrom and thereby leave BPA. The content of oxygen gas may be analyzed by any known method such as by gas chromatography or a trace oxygen analyzer adopting the electrochemical method.

The melting of the adduct is preferably performed at a temperature of 115°–180° C., more preferably 120°–150° C., and a pressure of 1.0–5.0 atm (absolute), more preferably 1.0–1.9 atm, using a vessel equipped with a suitable heater. The melted adduct is then transferred to a vaporization zone such as a distillation tower or a liquid film-type distillation device where phenol is vaporized and removed from the melted adduct. The vaporization zone is suitably of a multi-stage type. The vaporization is preferably performed at a temperature of 160°–200° C., more preferably 170°–185° C., under a reduced pressure of generally 100 Torr or less, preferably 5–40 Torr. When a multi-stage type vaporization is adopted, the final stage is operated under these conditions.

It is preferred that the removal of phenol by vaporization be carried out by first distilling phenol using a laminar flow type evaporator, followed by steam stripping for the removal of residual phenol. The steam stripping may be performed with a steam feed amount providing a steam to BPA weight ratio of 1:50 to 1:5, preferably 1:25 to 1:10.

The BPA product obtained by the above process has a purity of 99.95% or more and good color characteristics, such as an APHA color of 20 or less. Such a high grade BPA may be suitably used in the field of optics and may be utilized as a raw material for the production of polycarbonate resins and epoxy resins.

SECOND EMBODIMENT

Similar to the above first embodiment, the second embodiment uses, as a raw material, a crystalline adduct of BPA and phenol which has an APHA color of not greater than 15 and which shows a pH of 4.9–5.5 when dissolved in an aqueous methanol solution having a pH of 5 in a concentration of 4 g per ml of water. The raw material adduct may be a mixture of free phenol and BPA/phenol adduct. The raw material adduct is mixed with an aliphatic carboxylic acid to obtain a mixture containing 1–100 ppm of the aliphatic carboxylic acid based on the weight of the adduct. The mixture is then heated to melt the adduct and to vaporize phenol under a reduced pressure.

When melted BPA is contacted with air for a long period of time or when melted BPA is subjected to a high temperature, BPA tends to color. The aliphatic carboxylic acid serves to prevent BPA from coloring during the vaporization of phenol from the melted adduct. Any aliphatic carboxylic acid may be used as long as it can prevent the coloring of BPA. Examples of suitable aliphatic acids include formic acid, glycollic acid, oxalic acid, citric acid, lactic acid, malic acid, glyceric acid and tartaric acid. These acids are decomposed or isomerized at a temperature of about 160° C. or more and exhibit an excellent color-preventing effect on BPA. Substances other than aliphatic carboxylic acids, such as oxalic acid esters, ammonium oxalate, terephthalic acid and sodium hydrogen phosphate are not effective to prevent the coloring of BPA. The aliphatic acid is used in an amount of 1–100 ppm by weight, preferably 5–50 ppm by weight, based on the amount of the crystalline adduct.

The mixture containing the adduct and the aliphatic carboxylic acid is heated at a temperature of 115°–180° C., preferably 120°–150° C. and a pressure of 1–5 atm, preferably 1–1.9 atm, to melt the adduct. The melting is preferably performed in an atmosphere having an oxygen content of 0.005% by volume or less, preferably 0.001 by volume or less. The above conditions are especially suited when oxalic acid or citric acid is used as the aliphatic carboxylic acid.

For the purpose of facilitating the melting of the adduct, the raw material adduct may be dissolved in a high grade, melted phenol (such as a hot melt of previously-described purified phenol) or in a melt of previously melted adduct.

The mixture of the adduct and the aliphatic carboxylic acid thus melted is then heated at a temperature of 130°–200° C. under a reduced pressure to vaporize and remove phenol from the mixture. Preferably, the melted mixture as a whole is maintained at a temperature of not greater than 185° C. while at least a portion thereof is heated at a temperature of 160° C. or more. A vaporization temperature of less than 130° C. is insufficient to obtain the color-preventing effect of the aliphatic carboxylic acid. Too high a temperature in excess of 185° C., on the other hand, is disadvantageous because the aliphatic acid tends to be colored. The pressure at which the vaporization is performed is preferably 100 Torr or less, more preferably 5–40 Torr. The vaporization is desirably carried out in an atmosphere having a low oxygen content of 0.005% by volume or less, preferably 0.001% by volume or less.

The BPA product thus obtained has a high quality and good color characteristics. The product is not colored upon being melted and has good storage stability. The aliphatic carboxylic acid is decomposed or vaporized during the evaporation step so that substantially no aliphatic carboxylic acid is detected in the BPA product.

THIRD EMBODIMENT

As described previously, a crystalline adduct of BPA and phenol is obtained by reacting acetone with a stoichiometrically excess amount of phenol in the presence of a strong acid catalyst, followed by crystallization of the resulting reaction product. The term "strong acid" is intended to refer to a substance having a dissociation constant of $10^{-3}$ or more such as sulfuric acid, hydrochloric acid or a sulfonic acid-type ion exchange resin. While the purity of the crystalline adduct can be improved by performing the crystallization in a multi-stage mode and/or by washing the adduct with purified phenol, a small amount of the acid catalyst is generally contained in the adduct. At an elevated temperature, the acid catalyst reacts with phenol and BPA to produce impurities including colored substances. The acid catalyst may also be removed by neutralization. However, it is not a rare case that the acid catalyst still remains in a trace amount in the adduct.

The third embodiment according to the present invention uses a crystalline adduct containing a trace amount of the above strong acid substance as a raw material. Thus, the raw material adduct to be used in this embodiment has an APHA color of not greater than 15, contains a strong acid generally in an amount of not greater than 0.3 milligram equivalent per liter and shows a pH of smaller than 5 but not smaller than 4, perferably not smaller than 4.3, at 20° C. when dissolved in an aqueous methanol solution (water/methanol volume ratio: 5:100), whose pH has been adjusted by hydrochloric acid to 5, in a concentration of 4 g per ml of water. A crystalline adduct with an APHA color of 15 or less may be obtained by purification of a crude BPA/phenol adduct by repeated crystallization in a multi-stage crystallization mode and/or by washing with a purified phenol.

The raw material adduct is heated in the presence of a salt of an aliphatic carboxylic acid to melt the adduct and the melt is heated to vaporize phenol under a reduced pressure. The carboxylic acid salt serves to neutralize the strong acid contained in a trace amount in the raw material adduct with the simultaneous liberation of the corresponding free carboxylic acid. Thus, when the adduct is melted and the melt is heated for the removal of phenol by evaporation, no coloring of BPA takes place because of the absence of the strong acid which, as described previously, can react with BPA and phenol to yield impurities including colored substances. Moreover, the carboxylic acid formed in situ by reaction of the strong acid with the carboxylic acid salt serves to prevent the coloring of BPA. As a consequence, the BPA product obtained by the above method has improved color characteristics.

Any aliphatic acid salt may be used for the purpose of the present invention as long as it can neutralize the strong acid contained in the raw material adduct and can form free carboxylic acid capable of showing color-preventing effect on BPA. Preferably, an alkali metal, alkaline earth metal or ammonium salt of an acid selected from the group consisting of formic acid, glycolic acid, oxalic acid, citric acid, lactic acid, malic acid, glyceric acid and tartaric acid. These acids are decomposed or isomerized at a temperature of about 160° C. or more and exhibit an excellent color-preventing effect on BPA.

The carboxylic acid salt is used in an amount so that the mixture of the adduct and the carboxylic acid salt shows a pH of about 5 at 20° C. when dissolved in an aqueous methanol solution, which has a water/methanol volume ratio of 5:100 and whose pH is adjusted to 5 with hydrochloric acid, in a concentration of 4 g per ml of water. This amount is equivalent to neutralize the raw material crystalline adduct.

The use of an excess amount of the carboxylic acid salt is disadvantageous because it results in the coloring of the BPA product. When the amount of the carboxylic acid salt is insufficient to provide satisfactory color-preventing effect of free carboxylic acid, it is recommendable to add a free aliphatic carboxylic acid in addition to the carboxylic acid salt. The additional aliphatic acid is generally used in an amount so that the total amount of the additional aliphatic acid and the aliphatic acid derived from the aliphatic acid salt is 0.1–50 ppm by weight, preferably 1–30 ppm by weight, based on the amount of the crystalline adduct.

The melting of the adduct in the presence of the aliphatic carboxylic acid salt is performed at a temperature of 115°–180° C., preferably 120°–150° C. and a pressure of 1–5 atm, preferably 1–1.9 atm. The melting is preferably performed in an atmosphere having an oxygen content of 0.005% by volume or less, preferably 0.001 by volume or less. For the purpose of facilitating the melting of the adduct, the raw material adduct may be dissolved in a high grade, melted phenol (such as a hot melt of previously-described purified phenol) or in a melt of previously melted adduct.

The mixture of the adduct and the aliphatic carboxylic acid salt thus melted is then heated at a temperature of 130°–200° C. under a reduced pressure to vaporize and remove phenol from the mixture. Preferably, the melted mixture as a whole is maintained at a temperature of not greater than 185° C. while at least a portion thereof is heated at a temperature of 160° C. or more. A vaporization temperature of less than 130° C. is insufficient to obtain the color-preventing effect of the aliphatic carboxylic acid. Too high a temperature in excess of 185° C., on the other hand, is disadvantageous because the aliphatic acid tends to be colored. The pressure at which the vaporization is performed is preferably 100 Torr or less, more preferably 5–40 Torr. The vaporization is desirably carried out in an atmosphere having a low oxygen content of 0.005% by volume or less, preferably 0.001% by volume or less.

The BPA product thus obtained has a high quality and good color characteristics. The product is not colored upon being melted and has good storage stability.

FOURTH EMBODIMENT

The raw material adduct to be used in this embodiment has an APHA color of not greater than 15, preferably not greater than 10. and may be obtained by purification of a crude BPA/phenol adduct by repeated crystallization in a multi-stage crystallization mode and/or by washing with a purified phenol. The raw material adduct to be used in the above first to third embodiments may be used in this embodiment.

The crystalline adduct is fed to a melting zone to melt the adduct and the melted adduct is introduced into a separation zone to separate the melted adduct into phenol and BPA by evaporation of the phenol from the melted adduct in a manner known per se. In the fourth embodiment, the interior surfaces of the melting zone and the separation zone which are to be contacted with the melted adduct or the phenol separated from the melted adduct are previously washed with an organic solvent for the removal of oxygen gas entrapped in the interior surfaces so that the interior surfaces have an oxygen content of 10 mmoles or less per 1 $m^2$ thereof.

Conventional melting zone and separation zone generally have interior surfaces formed of a metal such as stainless steel SUS304, SUS316 or SUS316L. On such interior surfaces oxygen is bound in an amount of 30–60 mmol per 1 $m^2$ area thereof. The amount of oxygen deposited on a surface of a metal can be measured by various methods. For example, a method may be adopted in which a predetermined area of the metal surface is washed with a given amount of phenol. The phenol is then measured for its APHA color. Since $10^{-6}$ part by weight of oxygen is known to give an APHA color of 6 to one part by weight of phenol, the amount of the oxygen can be determined from the APHA color of the phenol used for washing the metal surface.

By removing oxygen entrapped on the interior surfaces of the melting and separation zones, the color characteristics of the BPA product is significantly improved. The removal of oxygen can be effected by washing the surfaces with an organic solvent having good affinity with oxygen, such as phenol, BPA or a mixture thereof. The washing may be carried out by injecting the organic solvent through a spray nozzle onto the interior surfaces at a temperature of 100°–200° C., preferably 120°–185° C., under ambient pressure in a non-oxidating atmosphere such as of nitrogen, argon or steam. If desired, reduce pressure may be used to effect the washing. The atmosphere in which the washing is performed is maintained in a low oxygen content of 0.01% by volume or less, preferably 0.005% by volume or less, more preferably 0.001% by volume or less. After completion of the washing, the organic solvent in the melting and separation zones is removed and the interior surfaces thereof are dried, if desired.

The removal of oxygen from the interior surfaces of the melting and separation zones should be performed until the oxygen content is decreased to 10 mmol, preferably 5 mmol, per 1 $m^2$ thereof. The melting zone is preferably an external heating-type, airtight vessel whose outer periphery is surrounded by a jacket for heating the vessel or an internal heating-type, airtight vessel within which a heating means such as a heater coil is disposed. As the separation zone, there may be suitably used a distillation tower, a steam-stripping device or a centrifugal thin film evaporator.

It is preferred that the interior surfaces of a pipe extending between the melting zone and the separation zone for the introduction of the melted adduct from the melting zone to the separation zone and of a pipe connected to the separation zone for discharging the BPA product therethrough be also subjected to the oxygen-removing treatment.

After the oxygen-removing treatment in respective zones and pipings has been completed, the raw material adduct is fed to the melting zone and the melted adduct is then introduced to the separating zone for the removal of phenol.

The melting of the adduct is performed at a temperature of 115°–180° C., preferably 120°–150° C. in an atmosphere having an oxygen content of 0.005% by volume or less, preferably 0.001 by volume or less. The evaporation in the separation zone is performed in one or more separating devices. The operating conditions in the final separating devices involve a temperature of 130°–200° C., preferably 170°–185° C., a reduced pressure of 1–100 Torr, preferably 5–40 Torr and an oxygen content in the atmosphere of 0.005% by volume or less, preferably 0.001% by volume or less.

The BPA product thus obtained has a high quality and good color characteristics.

Hitherto, the washing of the surfaces of interior surfaces of melting and separating zones so as to remove entrapped oxygen has not been carried out. As a result, colored product of BPA is unavoidably formed. Such a colored product fouls interior surfaces of lines and equipments which are provided downstream of the separataion zone and through which the colored product is passed. Once such fouling occurs, it is very troublesome to clean the fould portions.

FIFTH EMBODIMENT

The raw material adduct to be used in this embodiment has an APHA color of not greater than 15, preferably not greater than 10. The raw material adduct to be used in the above fourth embodiment may be used in this embodiment.

The crystalline adduct is fed to a melting zone to melt the adduct and the melted adduct is introduced into a separation zone to separate the melted adduct into phenol and BPA by evaporation of the phenol from the melted adduct in a manner known per se. The separation zone is provided with members, such as packing materials and trays, for increasing the area of the surface with which the melted crystalline adduct is to be contacted. The interior surface of the separation zone and the surface of the contact area-increasing members are previously treated for the removal of oxygen gas entrapped thereon so that the inside surface of the separation zone and the surface of the members have an oxygen content of 10 mmoles or less per 1 $m^2$ thereof.

Conventional separation zone generally has interior surfaces formed of a metal such as stainless steel SUS304, SUS316 or SUS316L. Contact area-increasing members to be provided within the separation zone are also formed of a similar metal. On surfaces of the inside of such separation zone and of contact area-increasing members, oxygen is bound in an amount of 30–60 mmol per 1 m$^2$ area thereof.

By removing oxygen entrapped on such surface, the color characteristics of the BPA product has been found to be significantly improved. The removal of oxygen can be effected by washing the surfaces with an organic solvent having good affinity with oxygen, such as phenol, BPA or a mixture thereof. The washing may be carried out by injecting the organic solvent through a spray nozzle onto the interior surfaces at a temperature of 100°–200° C., preferably 120°–185° C., under ambient pressure in a non-oxidating atmosphere such as of nitrogen, argon or steam or, if desired, under a reduced pressure. The atmosphere in which the washing is performed is maintained in a low oxygen content of 0.1% by volume or less, preferably 0.05% by volume or less.

The oxygen removal may also be effected by treatment with a reducing agent such as hydrazine.

The removal of oxygen from the interior surfaces of the separation zone and from the surfaces of the contact area-increasing members should be performed until the oxygen content is decreased to 10 mmol, preferably 5 mmol, per 1 m$^2$ area thereof.

It is preferred that interior surfaces of the melting zone, interior surfaces of a pipe extending between the melting zone and the separation zone for the introduction of the melted adduct from the melting zone to the separation zone and of a pipe connected to the separation zone for discharging the BPA product therethrough be also subjected to the oxygen-removing treatment.

After the oxygen-removing treatment in respective zones and pipings has been completed, the raw material adduct is fed to the melting zone and the melted adduct is then introduced to the separating zone for the removal of phenol.

The melting zone is preferably an external heating-type, airtight vessel whose outer periphery is surrounded by a jacket for heating the vessel or an internal heating-type, airtight vessel within which a heating means such as a heater coil is disposed. The melting of the adduct is performed at a temperature of 115°–180° C., preferably 120°–150° C., a pressure of 1.0–5.0 atm (absolute), preferably 1.0–1.9 atm in an atmosphere having an oxygen content of 0.005% by volume or less, preferably 0.001 by volume or less. For the purpose of facilitating the melting of the adduct, the raw material adduct may be dissolved in a high grade, melted phenol (such as a hot melt of previously-described purified phenol) or in a melt of previously melted adduct.

As the separation zone, there may be suitably used a distillation tower, a steam-stripping device or a thin film evaporator. These apparatuses generally have interior surfaces formed of a metal, such as a stainless steel SUS304, SUS316, SUS316L and are provided with contact area-increasing members. Heating means may be suitably disposed in the bottom of the distillation tower. As the contact area-increasing members, packing materials, plates and falling film walls formed of a metal such as a stainless steel SUS304, SUS316, SUS316L may be used. Examples of suitable packing materials include Raschig rings, pall rings, plates and perforated plates. Examples of trays include those in a bubble cap form or in a perforated plate form. These trays may be provided with downcommers, if desired.

The evaporation in the separation zone is performed in one or more evaporation towers inclusive of a steam stripping tower. Particularly preferred is the use of a combination of a first, ordinary evaporation tower without steam and a second, steam stripping evaporation tower. In this case, the melted adduct is heated in the first evaporation tower to remove a portion of the phenol by vaporization thereof under a reduced pressure without using steam. Phenol containing vapors are discharged overhead from the top of the first evaporation tower. A bottom fraction in the form of a melt is discharged from the bottom of the first tower and is introduced into the second evaporation tower where the remainder of phenol in the melt is removed by vaporization under a reduced pressure and stripped with steam. Vapors containing steam, phenol and a small amount of BPA are discharged overhead from the second evaporation tower while a BPA product is recovered from the bottom thereof. The BPA product thus obtained has a high quality and good color characteristics.

The evaporation in the first evaporation tower is performed at a temperature of 125°–200° C., preferably 130°–185° C., a reduced pressure of 100 Torr or less, preferably 5–40 Torr and an oxygen content in the atmosphere of 0.005% by volume or less, preferably 0.001% by volume or less. In the first evaporation tower, the melted adduct is treated so that 95–99.8% by weight, preferably 98–99.7% by weight, of the phenol contained therein is removed.

The evaporation in the second evaporation tower is performed at a temperature of 130°–200° C., preferably 160°–185° C., a reduced pressure of 100 Torr or less, preferably 5–40 Torr and an oxygen content in the atmosphere of 0.005% by volume or less, preferably 0.001% by volume or less. In the second evaporation tower, substantially all the phenol is removed so that the phenol content in the bottom BPA product is generally 200 ppm by weight or less, preferably 50 ppm by weight or less.

The vapors discharged overhead from the second evaporation tower is preferably introduced into a recovery zone to recover the phenol and BPA contained therein. This can be suitably performed with two stage cooling process which will be described hereinafter in connection with the eighth embodiment of the present invention.

SIXTH EMBODIMENT

The raw material adduct to be used in this embodiment preferably has an APHA color of not greater than 15, more preferably not greater than 10. The raw material adduct to be used in the above fourth embodiment may be used in this embodiment.

FIG. 1 depicts an apparatus suitable for carrying out the process according to the sixth embodiment of the present invention. Designated as 1 through 3 are first through third evaporators, respectively, each having a heater jacket 4 through which a heating medium is recirculated for heating the inside thereof. Each of the evaporators is preferably a thin film evaporator provided with rotating blades and adapted to form a falling liquid film on the inside periphery thereof by operation of the rotating blades.

The raw material adduct is melted or dissolved in purified phenol to form a liquefied adduct. The liquefied adduct preferably has an APHA color of 15 or less and contains 50-80% by weight, more preferably 60-75% by weight of BPA.

The liquefied adduct is introduced through a line 10 into the first, thin film evaporator 1 where the adduct is formed into a thin liquid film falling along the inside periphery thereof. During its downward flow, the liquefied adduct is heated by the heater jacket 4 so that phenol is vaporized. Vapors of phenol which contain a small amount of BPA vapors are discharged overhead from the first evaporator 1 through a line 11 and introduced into a recovery zone (not shown) for recovering phenol and BPA by condensation. The feed of the liquefied adduct through the line 10 preferably has a temperature of 120°-150° C. The evaporation in the first evaporator 1 is performed at a temperature of 160°-185° C., preferably 165°-175° C., and a pressure of 15-60 Torr, preferably 15-30 Torr.

The liquid product (first product) from which greater part of the phenol has been removed is discharged from the first evaporator 1 through a line 12 and is fed to the second evaporator 2. The first product in the line 12 contains 1-5% by weight of phenol. In the second evaporator 2, the first product is formed into a falling thin liquid film. While being heated by the heater jacket 4, the thin liquid film is brought into counter-current contact with a stripping gas introduced through a line 17. The stripping gas after the contact with the thin liquid film, which is composed of steam, phenol and BPA, is discharged overhead from the second evaporator 2 through a line 13. The evaporation in the second evaporator 2 is preferably performed at a temperature of 170°-185° C. and a pressure of 15 Torr or less, preferably 10-15 Torr.

The liquid product (second product) from which almost all of the phenol has been removed is discharged from the second evaporator 2 through a line 14 and is fed to the third evaporator 3. The second product in the line 14 preferably has a temperature of 170°-185° C. and contains 0.05-0.10% by weight, preferably 0.05-0.07% by weight of phenol.

In the third evaporator 3, the second product is formed into a downwardly flowing laminar flow which is brought into counter-current contact with steam introduced through a line 15 while being heated by the heater jacket 4. The steam after the contact with the thin liquid film containing stripped phenol and BPA is discharged overhead from the third evaporator 3 through the line 17 and is fed to the second evaporator 2 as the stripping gas, as described previously.

The evaporation in the third evaporator 3 is performed at a temperature of 170°-185° C. and a pressure of 15 Torr or less, preferably 10-15 Torr. The amount of steam fed through the line 15 to the third evaporator 3 is at least 3% by weight, preferably 4-6% by weight, based on the weight of the second product introduced through the line 14 into the third evaporator 3.

The overhead gas in the line 17 is composed of 0.8-1.2% by weight of phenol, 5-7% by weight of BPA and balance essentially steam. The liquid product (third product) from which substantially all of the phenol has been removed is discharged from the third evaporator 3 through a line 16 for recovery. The third product, namely the end product, has a content of phenol of 0.005% by weight or less and an APHA color of 20 or less.

The stripping gas discharged overhead from the second evaporator 2 through the line 13 is preferably introduced into a recovery zone to recover the phenol and BPA contained therein. This can be suitably performed with two stage cooling process which will be described hereinafter in connection with the eighth embodiment of the present invention.

In this embodiment, a liquefied adduct of BPA and phenol is first subjected to an evaporation treatment in the first evaporator 1 to obtain a first product containing BPA and 1-5% by weight of phenol. Since the first evaporator 1 is maintained at a temperature of 160°-185° C. and a pressure of 15-60 Torr, crystallization of BPA does not occur even when rapid vaporization of phenol causes cooling of the liquefied adduct in the form of a thin liquid film, ensuring smooth operation in the first evaporator 1.

The first product is then subjected to steam stripping in the second and third evaporators 2 and 3 to remove phenol therefrom. Since the content of phenol in the first product is as low as 1-5% by weight and since the second and third evaporators 2 and 3 are contiguously connected in series, it is possible to obtain highly pure BPA with a phenol content of less than 0.005% by weight by two step-steam stripping of the first product at a temperature of 170°-180° C. and a pressure of not higher than 15 Torr.

It is essential that the evaporation treatment should be performed at a temperature not higher than 185° C. in order to obtain BPA with good color characteristics, since otherwise colored impurities such as isopropenylphenol are apt to be produced. The BPA product obtained by the process of this embodiment has an APHA color of 20 or less and excellent color characteristics.

Since the steam stripping in the second evaporator 2 is performed using, as the stripping gas, the overhead gas obtained in the third evaporator 3, the process efficiency is improved. In addition, the present invention has a merit that the overall process can be carried out in a relatively short period of time (the residence time is generally 60-180 seconds). It is preferred that the evaporators 1-3 be arranged such that an upstream evaporator be located above the adjacent downstream evaporator, since the liquid to be treated can flow by gravity successively through the first to the third evaporators 1-3. By this, the overall process time can be shortened and the infiltration of environmental air into the evaporation system can be prevented.

SEVENTH EMBODIMENT

In the seventh embodiment according to the present invention, a crystalline adduct of BPA and phenol having an APHA color of not greater than 15, preferably not greater than 10, and showing a pH of 4.9-5.5 when dissolved in an aqueous methanol solution having a pH of 5 in a concentration of 4 g per ml of water is used as a starting material for the production of BPA. The crystalline adduct to be used in the above-described first embodiment may be suitably used.

The starting material adduct may be processed in the evaporation system shown in FIG. 1 and is treated in the same manner as that in the above sixth embodiment. In this embodiment, however, the evaporation in the first evaporator 1 is performed in an atmosphere having an oxygen concentration of 0.005% by volume or less. Such a substantially oxygen-free atmosphere may be produced by purging an inert gas such as nitrogen gas or argon gas into the first evaporator 1 before the start of the process. It is effective to repeat evacuation and purging to obtain an oxygen-free atmosphere.

It is preferred that the liquefied adduct to be fed to the first evaporator 1 contain an aliphatic carboxylic acid serving as a coloring-preventing agent. The carboxylic acid may be added to the starting material adduct which is in the form of powder, melt, slurry or solution. When melted BPA is contacted with air for a long period of time or when melted BPA is subjected to a high temperature, BPA tends to color. The aliphatic carboxylic acid serves to prevent BPA from coloring during the vaporization of phenol from the melted adduct.

Any aliphatic carboxylic acid may be used as long as it can prevent the coloring of BPA. Examples of suitable aliphatic acids include formic acid, glycollic acid, oxalic acid, citric acid, lactic acid, malic acid, glyceric acid and tartaric acid. These acids are decomposed or isomerized at a temperature of about 160° C. or more and exhibit an excellent color-preventing effect on BPA. The aliphatic acid is used in an amount of 1–100 ppm by weight, preferably 5–50 ppm by weight, based on the amount of the crystalline adduct.

EIGHTH EMBODIMENT

In this embodiment, a gaseous mixture of steam, phenol and BPA maintained at a pressure of 30 Torr or less is treated to recover the phenol and BPA. Such a gaseous mixture may be obtained as an overhead gas by stripping phenol-containing BPA liquid with steam. The gas discharged from the second evaporator 2 through the line 13 is the typical example of such a gaseous mixture to be treated in the eighth embodiment.

The gaseous mixture is introduced into a first cooling zone maintained at a reduced pressure, where the gas is brought into counter-current contact with a first, liquid cooling medium to condense substantially all of the BPA and part of the phenol and thereby obtain a first gas phase composed of uncondensed steam and uncondensed phenol and a first liquid phase containing BPA and phenol inclusive of those condensed during the counter-current contact. The first cooling medium is phenol or BPA-containing phenol.

The first cooling zone is maintained at such a temperature that the steam is prevented from condensing while a portion of the phenol is condensed, generally at a temperature higher by 1°–50° C. than the solidifying point of phenol. More particularly, the temperature of the first cooling zone is maintained at 42°–90° C., preferably 45°–55° C. The pressure within the first cooling zone is maintained at 30 Torr or less, preferably 5–20 Torr, and can be the same as that used in the second evaporator 2 in FIG. 1. In the first cooling zone, at least 70% by weight, preferably at least 85% by weight of the phenol in the gaseous mixture feed is condensed and recovered. A part of the first liquid phase may be recycled to the first cooling zone as at least part of the first cooling medium.

The first cooling medium is used in the first cooling zone in an amount sufficient to cool the gaseous mixture to a predetermined temperature and generally in an amount of 5–10 parts by weight, preferably 5–6 parts by weight per part by weight of the gaseous mixture. The weight ratio of the BPA to the phenol in the liquid contained in bottom in the first cooling tower is generally adjusted to 0.05–0.20. preferably 0.08–0.14. Since phenol is present in large excess relative to BPA, BPA/-phenol adduct crystals are not formed in the first cooling zone even though the temperature therein is lower than the solidifying point of BPA.

The first gas phase containing uncondensed phenol is fed to a second cooling zone wherein the gas is brought into counter-current contact with a second, liquid cooling medium, which is an aqueous solution of phenol, to condense substantially all of the gas and thereby obtain a condensate-containing liquid, namely an aqueous phenol solution. Part of the aqueous phenol solution thus obtained may be recycled to the second cooling zone as at least part of the second cooling medium.

The concentration of the phenol in the second cooling medium is suitably selected with the consideration of the composition of the first gas phase to be treated and the conditions employed in the first cooling zone and, generally, 55–75% by weight. The pressure within the second cooling zone is maintained at 30 Torr or less, preferably 5–20 Torr, and may be the same as in the first cooling zone. The second cooling zone is maintained at such a temperature that substantially all of the first gas phase is condensed, generally at a temperature lower by 1°–10° C. than the condensation point of steam.

The second cooling medium is used in the second cooling zone in an amount sufficient to condense substantially all of the first gas phase and generally in an amount of 100–300 parts by weight, preferably 190–250 parts by weight per part by weight of the first gas phase introduced into the second cooling zone.

The first and second cooling zones may be any gas-liquid contacting apparatus, such as a packed tower or a spray tower. As the packing material to be used in the packed tower, there may be suitably use Raschig rings, pall rings and perforated plates, which are low in pressure loss.

Figure 2:
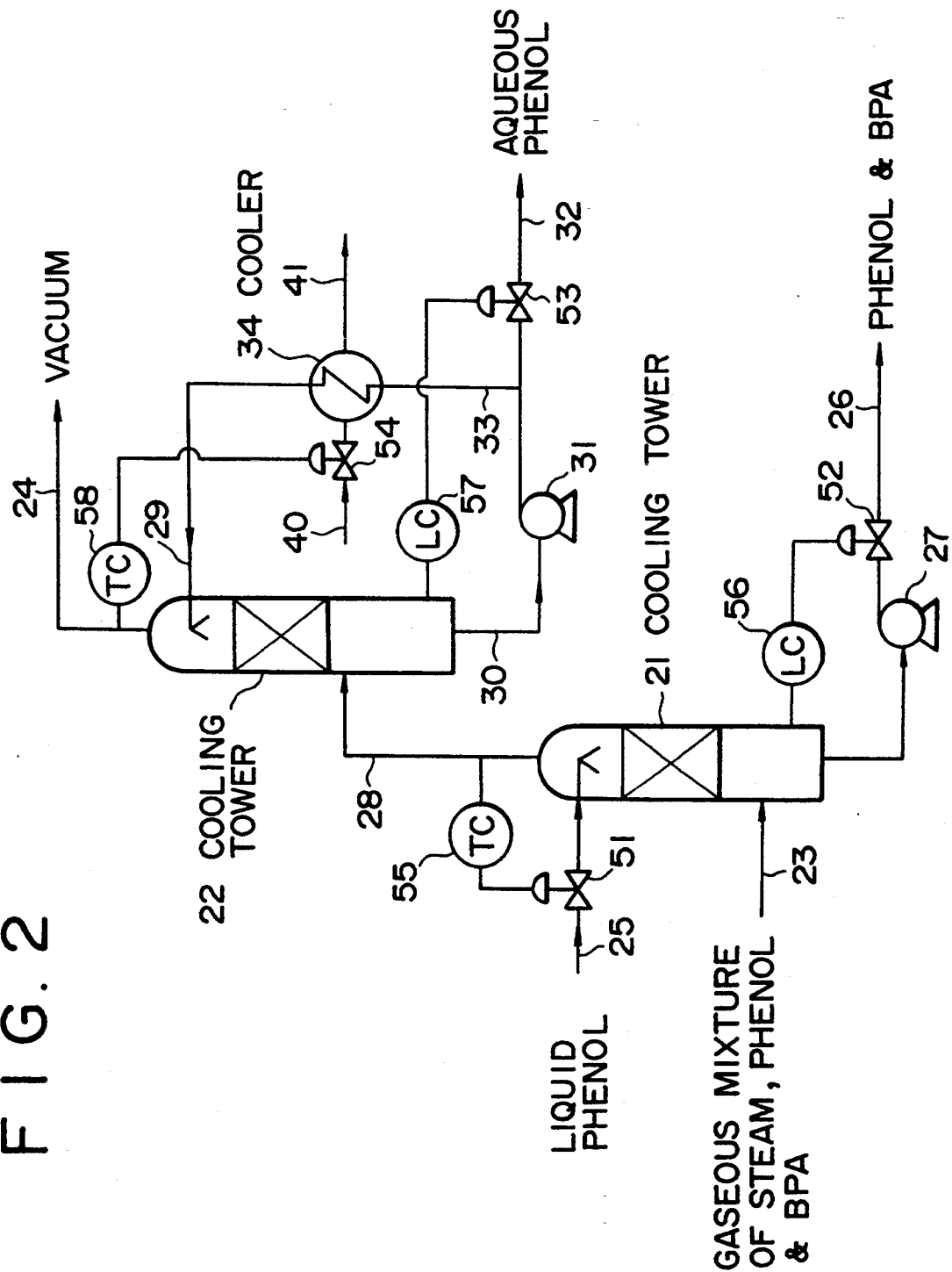
FIG. 2 is a schematic diagram showing an apparatus for carrying out a two-stage condensation process of the present invention.

FIG. 2 depicts one preferred apparatus useful for carrying out the above process. The reference numerals 21 and 22 designate first and second cooling towers, respectively. Designated as 23 is a line through which a feed of a gaseous mixture to be treated is introduced into the first cooling tower 21 and which may be connected to the line 13 of FIG. 1. An evacuation line 24 leading to a vacuum pump (not shown) through a cooler (not shown) is connected to the second cooling tower 22 to maintain the whole apparatus in a reduced pressure.

The gaseous mixture feed introduced into through the line 23 into the first cooling tower 21 is brought into counter-current contact with a first cooling medium (phenol or BPA-containing phenol) fed from the top of the tower 21 through a line 25 to condense part of the phenol and substantially entire BPA contained in the gaseous mixture feed. The resulting cooling medium in which the condensed BPA and phenol have been dissolved is discharged from the bottom of the tower 21 through a line 26 by the action of a pump 27. A portion of the liquid discharged through the line 26 may be recycled, after being cooled to a predetermined temperature, to the line 25 as at least part of the first cooling medium, if desired.

The gas mixture from which BPA and part of phenol have been removed is discharged from the top of the first cooling tower 21 through a line 28 and is introduced into the second cooling tower 22 where it is brought into counter-current contact with a second cooling medium (an aqueous solution of phenol) supplied through a line 29 and is substantially entirely condensed. The condensate is discharged together with the second cooling medium from the bottom of the tower 22 through a line 30 by the operation of a pump 31. A portion of the liquid in the line 30 is cooled in a cooler 34 by indirect heat exchange with a cooling medium, supplied through a line 40 and exhausted through a line 41, and is recycled through the line 29 to the second cooling tower 22 as the second cooling medium. The remainder portion of the liquid in the line 30 is discharged through a line 32 for recovery.

In FIG. 2, designated as 51-54 are flow control valves for controlling the flow rates of respective liquids in response to detection signals from temperature sensors 55 and 58 or liquid level sensors 56 and 57.

Figure 3:
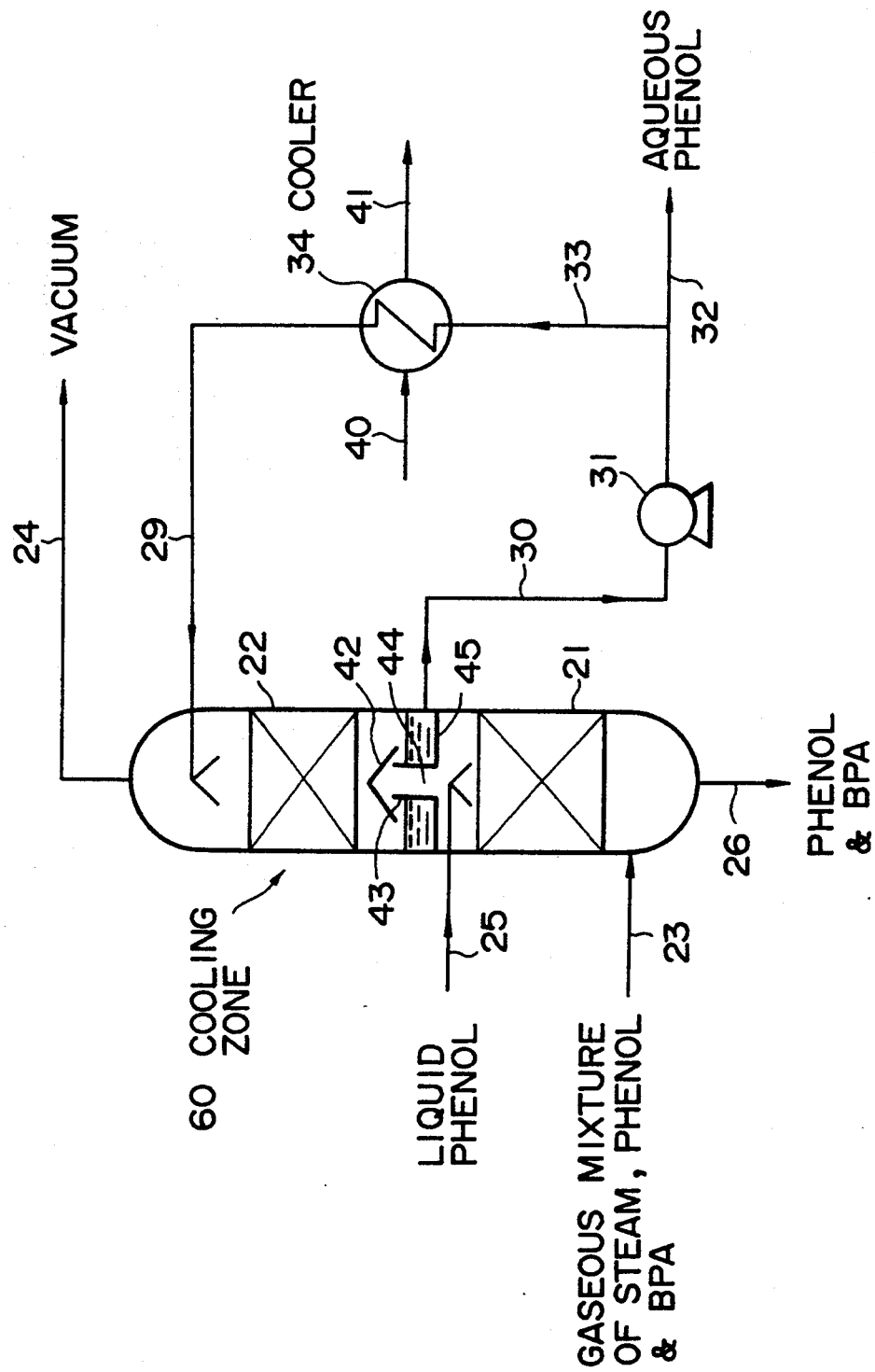
FIG. 3 is a schematic diagram showing another embodiment of the two-stage condensation process.

FIG. 3 illustrates another embodiment of an apparatus for carrying out the condensation treatment according to the eighth embodiment of the present invention. In FIG. 3, the same reference numerals as in FIG. 2 designate similar component parts and flow rate controlling members are omitted.

Designated generally as 60 is a cooling zone composed of vertically aligned first and second cooling towers 21 and 22. The first and second towers 21 and 22 are partitioned from each other by a partition plate 45 having an opening 44. A vertically upwardly extending cylinder 43 is connected to the opening 44 to define an annular, liquid collecting chamber above the partition plate 45 between the cylinder 43 and the inside wall of the cooling zone 60. The first and second towers are in fluid communication with each other through the opening 44. Designated as 42 is a guide plate to guide a liquid in the second cooling tower 22 into the liquid collecting chamber.

A gaseous mixture feed is introduced into through a line 23 into the first cooling tower 21 and is brought into counter-current contact with a first cooling medium fed through a line 25 to condense part of the phenol and substantially entire BPA contained in the gaseous mixture feed. The resulting cooling medium is discharged through a line 26. The gas mixture from which BPA and part of phenol have been removed is passed through the opening 44 to the second cooling tower 22 where it is brought into counter-current contact with a second cooling medium supplied through a line 29 and is condensed. The condensate is collected together with the second cooling medium in the annular chamber above the partition plate 45 and is discharged through a line 30 by the operation of a pump 31. A portion of the liquid in the line 30 is cooled in a cooler 34 by indirect heat exchange with a cooling medium, supplied through a line 40 and exhausted through a line 41, and is recycled through the line 29 to the second cooling tower 22 as the second cooling medium. The remainder portion of the liquid in the line 30 is discharged through a line 32 for recovery. An evacuation line 24 is connected to the top of the cooling zone 60 to maintain the first and second towers 21 and 22 in vacuum.

According to the process of the above eighth embodiment, the gaseous mixture of steam, phenol and BPA maintained in a reduced pressure of 30 Torr or less can be condensed without increasing the pressure. Though the condensation is carried out at a low pressure of 30 Torr or less and a low steam condensation temperature, no crystals of BPA or phenol are formed. Thus, the condensation treatment can be performed without bringing about reduction of cooling efficiency of the coolers or clogging thereof by deposition of solids. Further, the condensation treatment can condense all of the components of the gaseous mixture so that substantially no vapors of these components are passed to the vacuum pump. This is advantageous from the standpoint of installation costs and energy consumption because it is not necessary to use a vacuum pump with a large displacement capacity.

The gas mixture to be treated in accordance with this eighth embodiment may additionally contain phenol derivatives such as isopropenyl phenol. Such phenol derivatives are recovered toghether with phenol.

The following examples will further illustrate the present invention.

EXAMPLE 1

First Embodiment

Phenol was reacted with acetone in the presence of an acid catalyst to obtain a mixture containing BPA, phenol and impurities. The mixture was crystallized repeatedly to obtain a crystalline adduct of BPA and phenol having an APHA color of 5 and showing pH of 5.05 when dissolved in an aqueous methanol solution having pH of 5.0. This adduct was placed in a closed vessel and melted at 130° C. under 1.20 atm (absolute) in an atmosphere having an oxygen content of 0.001% by volume. The melted adduct was fed to an evaporator and heated at 180° C. in an atmosphere having an oxygen content of 0.001% by volume to vaporize and remove phenol. Subsequently, while maintaining the temperature and oxygen content in the evaporator at 180° C. and 0.003% by volume, respectively, steam was fed to the evaporator to strip the remaining phenol, thereby obtaining BPA having a purity of more than 99.96% by weight, a phenol content of less than 30 ppm by weight and an APHA color of 20.

COMPARATIVE EXAMPLE 1

Example 1 was repeated in the same manner as described except that the oxygen content in the evaporator during the evaporation and stripping steps was maintained at 0.006% by volume. The BPA thus obtained had a purity of more than 99.96% by weight, a phenol content of less than 30 ppm by weight and an APHA color of 65.

COMPARATIVE EXAMPLE 2

Example 1 was repeated in the same manner as described except that a crystalline adduct having an APHA color of 10 and showing pH of 4.85 when dissolved in an aqueous methanol solution having pH of 5.0. The BPA thus obtained had a purity of more than 99.90% by weight, a phenol content of less than 50 ppm by weight and an APHA color of 40.

COMPARATIVE EXAMPLE 3

Example 1 was repeated in the same manner as described except that a crystalline adduct having an APHA color of 20 and showing pH of 5.05 when dissolved in an aqueous methanol solution having pH of 5.0. The BPA thus obtained had a purity of more than 99.96% by weight, a phenol content of less than 30 ppm by weight and an APHA color of 45.

EXAMPLE 2

Example 1 was repeated in the same manner as described except that the oxygen content of the atmosphere in which the melting, evaporation or steam stripping was performed was changed as shown in Table 1. The APHA color, phenol content and pH of the BPA product are also shown in Table 1.

TABLE 1

| | Oxygen Content (vol %) | | | BPA Product | | |
|---|---|---|---|---|---|---|
| Experimen No. | Melting Step | Evaporation Step | Steam Stripping Step | APHA color | Phenol content | Purity |
| 1 | 0.0001 | 0.0001 | 0.0002 | 10 | <30 | >99.96 |
| 2 | 0.0005 | 0.0005 | 0.0010 | 10 | <30 | >99.96 |
| 3 | 0.0015 | 0.0015 | 0.0040 | 25 | <30 | >99.96 |
| 4 | 0.0020 | 0.0020 | 0.0040 | 30 | <30 | >99.96 |
| 5 | 0.0025 | 0.0025 | 0.0045 | 30 | <30 | >99.96 |
| 6* | 0.0030 | 0.0030 | 0.0055 | 40 | <30 | >99.96 |

*Comparative Experiment

EXAMPLE 3

Second Embodiment

Phenol was reacted with acetone in the presence of an acid catalyst to obtain a mixture containing BPA, phenol and impurities and having an APHA color of 50. The mixture was crystallized repeatedly to obtain a slurry containing crystalline adduct of BPA and phenol. The slurry was filtered under a reduced pressure to obtain adduct crystals. The crystals were then washed with 2.5 times the weight of purified phenol (hereinafter described) to obtain high purity adduct having an APHA color of 5-10 and showing pH of 5.05 when dissolved in an aqueous methanol solution having pH of 5.0. This adduct was mixed with an additive as shown in Table 2 to obtain a mixture having a content of the additive of 20 ppm by weight. The mixture was melted at 150° C. in an atmosphere having an oxygen content of 0.0010% by volume. The melt was subjected to an evaporation treatment at 175° C. and 10 Torr in an atmosphere having an oxygen content of 0.0010% by volume to vaporize and remove phenol and thereby obtain a BPA product having a phenol content of less than 30 ppm.

The purified phenol used for washing the crystals had an APHA color of 6 and was obtained by contacting industrial grade phenol (water content: 0.1% by weight, impurity content: 0.05% by weight) with a strong-acid ion exchange resin (Amberlite IR-118H+ manufactured by Rohm & Haas Company) at 80° C. for 50 minutes, followed by distillation at a distillation tower bottom temperature of 175° C. and a tower top pressure of 560 Torr.

The BPA product was then tested for its thermal stability in accordance with the following two methods to evaluate its color characteristics. The results are shown in Table 2.

Stability Test (I)
Test sample is maintained at 175° C. for 2 hours in air. The APHA color is measured before and after the heat treatment.

Stability Test (II)
Test sample is maintained at 175° C. for 2 hours while continuously feeding air. After the heat treatment, the APHA color is measured.

TABLE 2

| | | APHA Color | | |
|---|---|---|---|---|
| | | Test (I) | | Test (II) |
| Experiment No. | Additive | Before Heat Treatment | After Heat Treatment | After Heat Treatment |
| 1 | Lactic Acid | 10 | 15 | 30 |
| 2 | Oxalic Acid | 10 | 15 | 30 |
| 3 | Glyceric Acid | 10 | 15 | 30 |
| 4 | Citric Acid | 10 | 15 | 25 |
| 5 | Malic Acid | 10 | 15 | 25 |
| 6* | Ammonium Oxalate | 10-15 | 15 | 40 |
| 7* | Magnesium Phosphate | 20 | 30 | 70 |
| 8* | Terephthalic Acid | 10-15 | 20 | 50-60 |
| 9* | Ethylene Glycol | 20-25 | 40 | 70-80 |
| 10* | Dimethyl Oxalate | 10-15 | 15-20 | 50 |
| 11* | Sodium Hypophosphite | 20-25 | 50 | 70 |
| 12* | — | 10-15 | 20 | 35-40 |

*Comparative Experiment

COMPARATIVE EXAMPLE 4

Example 3, Experiments Nos. 2, 4 and 5 were repeated in the same manner as described except that a BPA/phenol adduct having an APHA color of 5-10 and showing pH of 4.85 when dissolved in an aqueous methanol solution having pH of 5.0 was used in place of the adduct showing pH of 5.05. The resulting BPA products had a phenol content of 50 ppm by weight and the thermal stability shown in Table 3.

TABLE 3

| | | APHA Color | | |
|---|---|---|---|---|
| | | Test (I) | | Test (II) |
| Experiment No. | Additive | Before Heat Treatment | After Heat Treatment | After Heat Treatment |
| 1 | Malic Acid | 20-25 | 30-35 | 60 |
| 2 | Oxalic Acid | 20 | 25-30 | 50-55 |
| 3 | Citric Acid | 20 | 20-25 | 55-60 |

EXAMPLE 4

Third Embodiment

Phenol was reacted with acetone in the presence of an acid catalyst to obtain a mixture containing BPA, phenol and impurities and having an APHA color of 50. The mixture was crystallized repeatedly to obtain an crystalline adduct having an APHA color of 5-10 and showing pH of 4.85 when dissolved in an aqueous methanol solution having pH of 5.0. This adduct was mixed with an additive as shown in Table 4 to obtain a mixture having a content of the additive of about 1 ppm by weight (Experiments Nos. 1-5; the amount to neutralize strongly acidic substances contained in the adduct) or about 20 ppm by weight (Experiments Nos. 6-9). The mixture was melted at 150° C. in an atmosphere having an oxygen content of 0.0010% by volume. The melt was subjected to an evaporation treatment at 175° C. and 10 Torr in an atmosphere having an oxygen content of 0.0010% by volume to vaporize and remove phenol and thereby obtain a BPA product having a phenol content of less than 30 ppm.

The BPA product was then tested for its thermal stability in accordance with the following two methods to evaluate its color characteristics. The results are shown in Table 4.

Stability Test (I)
Test sample is maintained at 175° C. for 2 hours in air. The APHA color is measured before and after the heat treatment.

Stability Test (II)

Test sample is maintained at 175° C. for 2.5 hours while continuously feeding air. After the heat treatment, the APHA color is measured.

TABLE 4

| Experiment No. | Additive | APHA Color | | |
|---|---|---|---|---|
| | | Test (I) | | Test (II) |
| | | Before Heat Treatment | After Heat Treatment | After Heat Treatment |
| 1 | Sodium Formate | 10-15 | 20 | 30-35 |
| 2 | Sodium Citrate | 10-15 | 20 | 30-35 |
| 3 | Sodium Malate | 10-15 | 20 | 35-40 |
| 4 | Sodium Acetate | 10-15 | 20 | 35-40 |
| 5 | Monoammonium Oxalate | 10-15 | 20 | 35-40 |
| 6* | Malic Acid | 20-25 | 30-35 | 60 |
| 7* | Oxalic Acid | 20 | 25-30 | 50-55 |
| 8* | Citric Acid | 20 | 20-25 | 55-60 |
| 9* | — | 25 | 40-45 | 70 |

*Comparative Experiment

EXAMPLE 5

Example 4 was repeated in the same manner as described except that a BPA/phenol adduct having an APHA color of 5-10 and showing pH of 4.22 when dissolved in an aqueous methanol solution having pH of 5.0 was used in place of the adduct showing pH of 4.85. The resulting BPA had the thermal stability shown in Table 5. The amount of the additive used in Experiments Nos. 1 and 2 was about 4 ppm which neutralized strongly acidic substances containing in the adduct. Citric acid was used in an amount of 20 ppm by weight in Experiment Nos. 3.

TABLE 5

| Experiment No. | Additive | APHA Color | | |
|---|---|---|---|---|
| | | Test (I) | | Test (II) |
| | | Before Heat Treatment | After Heat Treatment | After Heat Treatment |
| 1 | Magnesium Citrate | 10-15 | 20 | 30-35 |
| 2 | Sodium Malate | 10-15 | 25 | 35-40 |
| 3* | Citric Acid | 30 | 60 | 75 |
| 4* | — | 35 | 75 | 90 |

*Comparative Expreiment

EXAMPLE 6

Fourth Embodiment

First, a closed, melting vessel formed of a stainless steel (SUS304) and surrounded by a heating jacket was used as a melting zone for melting a BPA/phenol adduct. A crystalline adduct feed line was connected to an upper portion of the melting vessel. One end of a melt transferring line was connected to a bottom portion of the melting vessel with the other end of the transferring line being connected to an intermediate portion of a stripping tower formed of a stainless steel (SUS 304). The stripping tower was provided with a phenol vapor exhausting line at an upper portion thereof and with a BPA melt discharging line at a bottom portion thereof. Each of the above-described lines was formed of a stainless steel (SUS304).

The interior surfaces of the melting vessel, stripping tower, the melt transferring line extending therebetween and the BPA melt discharge line were then washed as follows.

(1) Washing of Melting Vessel

A spray nozzle was inserted into the melting vessel and phenol at 130° C. was sprayed through the nozzle over the interior surface of the vessel. Thereafter, a 65:35 (wt/wt) phenol/BPA mixture at 150° C. was sprayed through the nozzle for sufficiently washing the interior surface.

(2) Washing of Stripping Tower

A spray nozzle was fitted to an upper portion in the inside of the tower. Phenol at 130° C. was sprayed through the nozzle to wash a major, intermediate portion of the interior surface of the tower. Thereafter, phenol at 130° C. was passed through the tower and then a 65:35 phenol/BPA mixture at 150° C. was passed therethrough. Finally, the phenol/BPA mixture was passed through the tower at 180° C. under 10 Torr.

(3) Washing of Transferring and Discharging Lines

Phenol at 130° C. was passed through the transferring and discharging lines while preventing air bubbles from remaining in the lines.

As a consequence of the washing, the content of oxygen on the interior surfaces of the melting vessel, stripping tower and transferring and discharging lines was reduced to 5 mmol or less per 1 $m^2$ area thereof.

Using the thus washed devices, a crystalline adduct of BPA and phenol was treated to remove phenol and to obtain a BPA product having an APHA color of 10. The crystalline adduct was as obtained as follows.

Phenol was reacted with acetone in the presence of an acid catalyst to obtain a mixture containing BPA, phenol and impurities and having an APHA color of 50. The mixture was crystallized repeatedly to obtain adduct crystals. The crystals were then washed with 2.5 times the weight of purified phenol (hereinafter described) to obtain a crystalline adduct having an APHA color of 5. The purified phenol used for washing the crystals had an APHA color of 6 and was obtained by contacting industrial grade phenol (water content: 0.1% by weight, impurity content: 0.05% by weight) with a strong-acid ion exchange resin (Amberlite IR-118H+, manufactured by Rohm & Haas Company) at 80° C. for 50 minutes, followed by distillation at a distillation tower bottom temperature of 175° C. and a tower top pressure of 560 Torr.

The melting vessel and the stripping tower were operated under the following conditions:

Melting Vessel
 Temperature: 130° C.
 Pressure: Ambient pressure
 Oxygen Content in the Atmosphere: 0.0005% by volume Stripping Tower
 Temperature: 175° C.
 Pressure: 10 Torr
 Oxygen Content in the Atmosphere: 0.0015% by volume

COMPARATIVE EXAMPLE 5

Example 6 was repeated in the same manner as described except that the melting vessel, the stripping tower, the transferring and discharging lines were not washed. The BPA product obtained had an APHA color of 80.

EXAMPLE 7

Fifth Embodiment

First, a closed, melting vessel formed of a stainless steel (SUS316) and surrounded by a heating jacket was used as a melting zone for melting a BPA/phenol adduct. A crystalline adduct feed line was connected to an upper portion of the melting vessel. A first, melt transferring line was connected at its one end to a bottom portion of the melting vessel with the other end of thereof being connected to an intermediate portion of a first packed tower formed of a stainless steel (SUS 304). The first packed tower was provided with a phenol vapor exhausting line at an upper portion thereof and with a second, melt transferring line at a bottom portion thereof. The second transferring line is connected to an intermediate portion of a second packed tower formed of a stainless steel (SUS304) and provided with a stripped gas exhausting line at an upper portion of thereof and with steam feed and melt discharge lines at bottom portions thereof. Each of the above-described lines was formed of a stainless steel (SUS304). Each of the first and second packed towers was provided with packing materials formed of a stainless steel (SUS316) and a heater coil at the bottom thereof. The stripped gas exhausting line was connected to a condensation device as shown in FIG. 2.

The interior surfaces of the melting vessel, first and second packed towers, the first and second transferring lines and the melt discharge line were then washed as follows.

(1) Washing of Melting Vessel

A spray nozzle was inserted into the melting vessel and phenol at 130° C. was sprayed through the nozzle over the interior surface of the vessel. Thereafter, a 65:35 (wt/wt) phenol/BPA mixture at 150° C. was sprayed through the nozzle for sufficiently washing the interior surface.

(2) Washing of Packed Towers and Packing Materials

A spray nozzle was fitted to an upper portion in the inside of each of the first and second packed towers. Phenol at 130° C. was sprayed through the nozzle to wash a major, intermediate portion of the interior surface of each tower. Thereafter, phenol at 130° C. was passed through the tower and then a 65:35 phenol/BPA mixture at 150° C. was passed therethrough. Finally, the phenol/BPA mixture was passed through the tower at 180° C. under 10 Torr.

(3) Washing of First and Second Transferring Lines and Discharging Line

Phenol at 130° C. was passed through the first and second transferring lines and and the discharging line while preventing air bubbles from remaining in the lines.

As a consequence of the washing, the content of oxygen on the interior surfaces of the melting vessel, first and second packed towers, first and second transferring lines and the discharging line and on the surfaces of the packing materials was reduced to 5 mmol or less per 1 $m^2$ area thereof.

Using the thus washed devices, a crystalline adduct of BPA and phenol was treated to remove phenol and to obtain a BPA product having an APHA color of 10. The crystalline adduct was as obtained as follows.

Phenol was reacted with acetone in the presence of an acid catalyst to obtain a mixture containing BPA, phenol and impurities and having an APHA color of 50. The mixture was crystallized repeatedly to obtain adduct crystals. The crystals were then washed with 2.5 times the weight of purified phenol (hereinafter described) to obtain a crystalline adduct having an APHA color of 5. The purified phenol used for washing the crystals had an APHA color of 6 and was obtained by contacting industrial grade phenol (water content: 0.1% by weight, impurity content: 0.05% by weight) with a strong-acid ion exchange resin (Amberlite IR-118H+, manufactured by Rohm & Haas Company) at 80° C. for 50 minutes, followed by distillation at a distillation tower bottom temperature of 175° C. and a tower top pressure of 540 Torr.

The melting vessel and the first and second packed towers were operated under the following conditions:

Melting Vessel
  Temperature: 130° C.
  Pressure: Ambient pressure
  Oxygen Content in the Atmosphere: 0.0005% by volume First Packed Tower
  Temperature: 170° C.
  Pressure: 10 Torr
  Oxygen Content in the Atmosphere: 0.0015% by volume Second Packed Tower
  Temperature: 180° C.
  Pressure: 10 Torr
  Oxygen Content in the Atmosphere: 0.0002% by volume
  Amount of Steam Feed: 0.08 kg per 1 kg of the melt feed The stripped gas exhausted from the second packed tower was introduced into a condensation apparatus as shown in FIG. 2 and treated under the following conditions.

Stripped Gas in Line 23
  Composition: 25% by weight of BPA, 25% by weight of phenol and 50% by weight of steam
  Temperature: 180° C.
  Pressure: 10 Torr Liquid Phenol in Line 25
  Temperature: 50° C.
  Amount: 6 parts by weight per part by weight of the stripped gas Recovery Rate in First Cooling Tower 21
  BPA: 100%

Uncondensed Gas in Line 28
  Temperature: 51° C.
  Pressure: 10 Torr
  Composition: 65% by weight of phenol and 35% by weight of steam Cooling Medium in Line 29
  Composition: aqueous phenol
  Temperature: 9° C.
  Amount: 190 parts by weight per part by weight of the uncondensed gas fed through the line 28

Recovery Rate in Second Cooling Tower 22
  Phenol: 100%
  Steam: 100%

EXAMPLE 8

Example 7 was repeated in the same manner as described except that the melting vessel, first and second transferring lines and the discharge line were not washed. The BPA product obtained had an APHA color of 15.

COMPARATIVE EXAMPLE 6

Example 7 was repeated in the same manner as described except that the melting vessel, the first and second packed towers, the first and second transferring lines, the packed materials in the first and second packed towers and the discharging line were not washed. The BPA product obtained had an APHA color of 200.

COMPARATIVE EXAMPLE 7

Example 7 was repeated in the same manner as described except that the first and second packed towers and the packed materials in the first and second packed towers were not washed. The BPA product obtained had an APHA color of 200.

EXAMPLE 9

Sixth Embodiment

Phenol was reacted with acetone in the presence of an acid catalyst to obtain a mixture containing BPA, phenol and impurities. The mixture was crystallized repeatedly to obtain a crystalline adduct of BPA and phenol having an APHA color of 5. This was diluted with purified phenol and heated at 130° C. to obtain a phenol solution containing 30% by weight of BPA.

The phenol solution was then treated using the apparatus shown in FIG. 1. The operation conditions were as summarized below.

First Evaporator 1
 Temperature of Heater 4: 170° C.
 Pressure: 20 Torr
Second Evaporator 2
 Temperature of Heater 4: 180° C.
 Pressure: 10 Torr
Third Evaporator 3
 Temperature of Heater 4: 180° C.
 Pressure: 10 Torr
Content of Phenol
 In Line 12: 2.7% by weight
BPA Product in Line 16
 Phenol Content: 23 ppm by weight
 APHA Color: 20
Amount of Steam Fed through Line 15
 0.04 part by weight per part by weight of the BPA feed through the line 14

COMPARATIVE EXAMPLE 8

When the first evaporator 1 in Example 9 was operated at 190° C. under 10 Torr, the phenol content in the BPA in the line 12 was 7% by weight. Thus, the evaporation operation was not able to be performed in a stable manner.

COMPARATIVE EXAMPLE 9

When the temperature of the heater 4 in each of the second and third evaporators 2 and 3 was increased to 200 C in Example 9, the BPA product in the line 16 had an APHA color of 45 and a phenol content of 70 ppm by weight.

EXAMPLE 10

Seventh Embodiment

Phenol was reacted with acetone in the presence of an acid catalyst to obtain a mixture containing BPA, phenol and impurities. The mixture was crystallized repeatedly to obtain a crystalline adduct of BPA and phenol having an APHA color of 5 and showing pH of 5.05 when dissolved in an aqueous methanol solution having pH of 5.0. This was diluted with purified phenol and heated at 130° C. to obtain a phenol solution containing 30% by weight of BPA.

The phenol solution was then treated using the apparatus shown in FIG. 1. The operation conditions were as summarized below.

First Evaporator 1
 Temperature of Heater 4: 170° C.
 Pressure: 20 Torr
 Oxygen content in the atmosphere: 0.0010% by volume
Second Evaporator 2
 Temperature of Heater 4: 180° C.
 Pressure: 10 Torr
 Oxygen content in the atmosphere: 0.0030% by volume
Third Evaporator 3
 Temperature of Heater 4: 180° C.
 Pressure: 10 Torr
 Oxygen content in the atmosphere: 0.0030% by volume
BPA Product in Line 16
 Phenol Content: 29 ppm by weight
 APHA Color: 15
Amount of Steam Fed through Line 15
 0.04 part by weight per part by weight of the BPA feed through the line 14

EXAMPLE 11

Example 10 was repeated in the same manner as described except that an additive as shown in Table 6 was mixed with the phenol solution in an amount providing a mixture having a content of the additive of 20 ppm by weight. The BPA product obtained in the line 16 had a phenol content of 27 ppm and an APHA color of 10. The BPA product was then tested for its thermal stability in accordance with the following two methods to evaluate its color characteristics. The results are shown in Table 6.

Stability Test (I)

Test sample is maintained at 175° C. for 2 hours in air. The APHA color is measured before and after the heat treatment.

Stability Test (II)

Test sample is maintained at 175° C. for 2 hours while continuously feeding air. After the heat treatment, the APHA color is measured.

TABLE 6

| Experiment No. | Additive | APHA Color Test (I) Before Heat Treatment | APHA Color Test (I) After Heat Treatment | APHA Color Test (II) After Heat Treatment |
|---|---|---|---|---|
| 1 | Lactic Acid | 10 | 15 | 30 |
| 2 | Oxalic Acid | 10 | 15 | 30 |
| 3 | Glyceric Acid | 10 | 15 | 30 |
| 4 | Citric Acid | 10 | 15 | 25 |
| 5 | Malic Acid | 10 | 15 | 25 |

EXAMPLE 12

Phenol was reacted with acetone in the presence of an acid catalyst to obtain a mixture containing BPA, phenol and impurities and having an APHA color of 50. The mixture was crystallized repeatedly to obtain a slurry containing crystalline adduct of BPA and phenol. The slurry was filtered under a reduced pressure to obtain adduct crystals. The crystals were then washed with 2.5 times the weight of purified phenol (hereinafter described) to obtain high purity adduct having an APHA color of 5–10 and showing pH of 5.05 when dissolved in an aqueous methanol solution having pH of 5.0. This adduct (1 part by weight) was mixed with purified phenol (1 part by weight) and melted at 130° C. to obtain a melt. The melt (pH 5.05) was then treated in the same manner as that in Example 1 obtain a BPA product having a purity of 99.96% by weight, a phenol content of less than 30 ppm and an APHA color of 15.

The purified phenol used for washing the crystals had an APHA color of 6 and was obtained by contacting industrial grade phenol (water content: 0.1% by weight, impurity content: 0.05% by weight) with a strong-acid ion exchange resin (Amberlite IR-118H+, manufactured by Rohm & Haas Company) at 80° C. for 50 minutes, followed by distillation at a distillation tower bottom temperature of 175° C. and a tower top pressure of 560 Torr.

What is claimed is:

1. A process of producing bisphenol A, comprising the steps of:
providing a crystalline adduct of bisphenol A and phenol which has an APHA color of not greater than 15 and which shows a pH of 4.9–5.5 when dissolved in an aqueous methanol solution having a pH of 5;
mixing said adduct with an aliphatic carboxylic acid to obtain a mixture containing 1–100 ppm of the aliphatic carboxylic acid based on the weight of said adduct; and
heating said mixture at a temperature of 130°–200° C. under a reduced pressure to vaporize and remove phenol from said mixture and thereby leave bisphenol A.

2. A process as claimed in claim 1 wherein said aliphatic carboxylic acid is selected from the group consisting of formic acid, glycollic acid, oxalic acid, citric acid, lactic acid, malic acid, glyceric acid and tartaric acid.

3. A process as claimed in claim 1, wherein said crystalline adduct has been subjected to recrystallization from phenol and washed with purified phenol.

4. A process of producing bisphenol A, comprising the steps of:
providing a crystalline adduct of bisphenol A and phenol which has an APHA color of not greater than 15, which contains a strong acid and which shows a pH of smaller than 5 but not smaller than 4 when dissolved in an aqueous methanol solution having a pH of 5;
mixing said adduct with a salt of an aliphatic carboxylic acid to obtain a mixture, said salt being used in an amount so that said mixture shows a pH of about 5 when dissolved in an aqueous methanol solution having a pH of 5; and
heating said mixture at a temperature of 130°–200° C. under a reduced pressure to vaporize and remove phenol from said mixture and thereby leave bisphenol A.

5. A process as claimed in claim 4 wherein said aliphatic carboxylic acid salt is an alkali metal, alkaline earth metal or ammonium salt of an acid selected from the group consisting of formic acid, glycollic acid, oxalic acid, citric acid, lactic acid, malic acid, glyceric acid and tartaric acid.

6. A process as claimed in claim 4, wherein said crystalline adduct has been subjected to recrystallization from phenol and washed with purified phenol.

* * * * *